United States Patent [19]
Wu

[11] Patent Number: 5,233,115
[45] Date of Patent: Aug. 3, 1993

[54] ETHYLENE OLIGOMERIZATION

[75] Inventor: An-hsiang Wu, Bartlesville, Okla.

[73] Assignee: Phillips Petroleum Company, Bartlesville, Okla.

[21] Appl. No.: 988,042

[22] Filed: Dec. 9, 1992

[51] Int. Cl.⁵ .............................................. C07C 2/02
[52] U.S. Cl. .................................. 585/521; 585/525; 585/527; 585/530; 585/531
[58] Field of Search ............... 585/521, 525, 527, 530, 585/531

[56] References Cited

U.S. PATENT DOCUMENTS

| | | | |
|---|---|---|---|
| 3,390,195 | 6/1968 | Chappell, III et al. | |
| 3,686,351 | 8/1972 | Mason | 585/531 |
| 3,736,264 | 5/1973 | Chawin | 585/527 |
| 4,482,640 | 11/1984 | Knudsen et al. | 502/155 |
| 4,503,279 | 3/1985 | Singleton | 585/525 |
| 4,716,138 | 12/1987 | Murray | 502/117 |
| 5,162,595 | 11/1992 | Wu | 585/527 |

*Primary Examiner*—Patrick P. Garvin
*Assistant Examiner*—E. D. Irzinski
*Attorney, Agent, or Firm*—William R. Sharp

[57] ABSTRACT

An ethylene oligomerization process is provided wherein ethylene is contacted with a nickel(II) halide compound, a phosphine compound, and a carboxylate compound in a solvent to produce a precursor reaction mixture, followed by contacting ethylene with the precursor reaction mixture and a borohydride compound to produce a product reaction mixture comprising the desired oligomerization product.

14 Claims, No Drawings

ETHYLENE OLIGOMERIZATION

This invention relates to a process for oligomerizing ethylene to an oligomerization product. The term "oligomerization product" as used herein and in the appended claims is defined as including olefinic oligomers of ethylene, i.e. $C_nH_{2n}$ where $n=4,6,8,10,\ldots$ The simpler notation of $C_n$ will be used hereafter to denote such oligomers.

Olefins, including α-olefins or 1-olefins, have become very important products in the chemical industry. Through hydroformylation, copolymerization and arylation/sulfonation, the 1-olefins become components of plasticizers, solvents, plastics, surfactants, synthetic lubricants, fatty acids, and detergents. Production of 1-olefins by oligomerizing ethylene has been previously investigated to a considerable extent, such as in processes employing nickel catalyzed oligomerization, but further development would be desirable in regard to achieving a desirable combination of productivity, selectivity to 1-olefins, and distribution (primarily $C_4$'s–$C_{10}$'s) of oligomers in the oligomerization product.

It is, therefore, an object of the invention to provide a process for oligomerizing ethylene which achieves the above-mentioned desired combination of results.

The above object is realized by a process for oligomerizing ethylene to an oligomerization product comprising: (a) contacting ethylene, a nickel(II) halide compound, a phosphine compound of the formula $PR_3$ where each R independently represents H or a $C_1$ to $C_{20}$ hydrocarbyl radical and where at least one R is not H, and a carboxylate compound of the formula R'COOM where R' is a $C_1$ to $C_{10}$ fluorinated hydrocarbyl radical having at least one fluorine atom and M is an alkali metal, wherein the ethylene is in a gaseous phase and the nickel(II) halide compound, phosphine compound, and carboxylate compound are in a solvent and in a liquid phase, thereby producing a precursor reaction mixture in a liquid phase; and (b) contacting, after step (a), ethylene in a gaseous phase, the precursor reaction mixture, and a borohydride compound of the formula $M'BH_{4-n}R_n''$ where $n=1,2$, or 3, M' is an alkali metal, and each R'' independently represents a $C_1$ to $C_{20}$ hydrocarbyl radical, thereby producing a product reaction mixture in a liquid phase comprising the oligomerization product.

As used herein and in the appended claims, the term "nickel(II) halide compound" is defined as having a molecular structure with a nickel atom at a valence state of +2 and at least two ligands which are halogen (Cl, Br, I, or F) atoms. Nickel(II) chloride compounds are preferred. The nickel(II) halide can have only the two halogen ligands ("anhydrous"), but can also be in a form which has additional ligands such as $H_2O$ or organic ligands complexed with the nickel atom. The latter compounds are generally preferred due to their stability, and include, for example, nickel(II) chloride hexahydrate and nickel(II) chloride dimethoxyethane.

Suitable phosphine compounds of the formula $PR_3$ where each R independently represents H or a $C_1$ to a $C_{20}$ hydrocarbyl radical and where at least one R is not H, include cyclohexylphosphine, dicyclohexylphosphine, tricyclohexylphosphine, tri-n-hexylphosphine, triethylphosphine, triisopropylphosphine, triisobutylphosphine, tri-n-butylphosphine, tri-t-butylphosphine, phenylphosphine, diphenylphosphine, triphenylphosphine, diphenylcyclohexylphosphine, diethylphenylphosphine, ortho-tolyldiphenylphosphine, di(orthotolyl)phenylphosphine, and tribenzylphosphine. Dicyclohexylphosphine has been found to give good results in terms of productivity, oligomer distribution, and selectivity to 1-olefins.

Suitable carboxylates of the formula R'COOM (where M is an alkali metal such as sodium, potassium, or lithium, and R' is a $C_1$ to $C_{10}$, preferably $C_1$ to $C_3$, fluorinated hydrocarbyl radical) include any of the alkali metal salts of fluorinated carboxylic acids such as trifluoracetic acid, heptafluorobutyric acid, difluoroacetic acid, and pentafluoropropionic acid. The presently preferred carboxylate is potassium trifluoroacetate.

Suitable borohydrides of the formula $M'BH_{4-n}R_n''$ (where $n=1,2$, or 3, M' is an alkali metal such as sodium, potassium, or lithium, and each R'' independently represents a $C_1$ to $C_{20}$ hydrocarbyl radical) include sodium triethylborohydride, sodium tri-sec-butylborohydride, potassium tri-sec-butylborohydride, potassium triethylborohydride, potassium triphenylborohydride, potassium trisiamylborohydride, lithium thexylborohydride, lithium dimethylborohydride, lithium thexyllimonylborohydride, lithium triethylborohydride, and lithium tri-sec-butylborohydride. Particularly preferred in accordance with the invention are those borohydrides of the above-mentioned formula where $n=3$ and R'' is a $C_1$ to $C_{12}$, preferably $C_1$ to $C_6$, alkyl radical. Sodium triethylborohydride is most preferred.

The preferred molar ratio of (i) the phosphine compound, (ii) the carboxylate compound, and (iii) the borohydride compound, respectively, to the nickel(II) halide compound are as follows: (i) about 0.1–5 to 1, most preferably about 0.8–1.2 to 1; (ii) about 0.1–5 to 1, most preferably about 0.8–1.2 to 1; and (iii) about 1–10 to 1, most preferably 1.5–2.5 to 1.

The solvent which is employed in the process of the invention can be any solvent in which the various reagents are adequately soluble to carry out the oligomerization reaction. Preferably, the solvent is a $C_1$–$C_{12}$ hydroxylated hydrocarbon having at least one hydroxyl group and selected from alcohols and phenols. Examples include n-propanol, 2-propanol, ethanol, phenol, 1,4-butanediol, trifluoroethanol, and 1,5-pentanediol. Alcohols are preferred as giving the best balance of productivity, oligomer distribution, and selectivity to 1-olefins.

The weight ratio of the total amount of solvent employed in the process to the combination of the nickel(II) halide compound, phosphine compound, carboxylate compound, and borohydride compound can be in the broad range of about $1-10^6$ to 1, most preferably in the range of about 5–10,000 to 1. The amount of solvent employed depends upon the cost, ease of oligomerization product recovery therefrom, reactor size, and other practical considerations.

The particular procedure by which the various reagents are contacted as in (a) and (b) above can take a variety of forms.

In accordance with step (a), the nickel(II) halide compound, phosphine compound, and the carboxylate compound in the solvent and in liquid phase can be contacted with ethylene in gaseous phase in a first vessel by agitating the liquid phase therein and pressuring the first vessel with the ethylene to a predetermined pressure.

In accordance with step (b), a solution of the borohydride compound (i.e. in a suitable hydrocarbon such as toluene) can be added to a second vessel, and either the precursor reaction mixture resulting from step (a) can be transferred from the first vessel to the second vessel or the borohydride solution can be transferred to the first vessel. In either case, the precursor reaction mixture and borohydride are preferably agitated in whichever vessel receives all liquid reagents and such vessel is pressured with ethylene to a predetermined reaction pressure.

The vessel in which step (b) is carried out can be an autoclave or other similar pressure reactor, and the vessel in which step (a) is carried out can be such a reactor or an associated addition vessel, depending on the particular procedure employed.

Pressure and temperature conditions in steps (a) and (b) are such that the ethylene is in a gaseous phase and the various reagents as in the solvent are in the liquid phase. Preferably, step (a) is carried out at a pressure of about 5 to 5,000 psig and a temperature of about 0° C. to about 100° C., most preferably at a pressure of about 20 to about 1000 psig and a temperature of about 20° C. to about 75° C. Step (b) is preferably carried out at a pressure of about 5 to about 5000 psig and a temperature of about 25° C. to about 125° C., most preferably at a pressure of about 200 to about 1000 psig and a temperature of about 50° C. to about 100° C.

With respect to time, step (a) is preferably carried out for a time of about 1 minute to about 2 hours, most preferably about 3 minutes to about 30 minutes. Step (b) is preferably carried out for a time of about 1 minute to about 15 hours, most preferably about 15 minutes to about 5 hours.

The oligomerization product as contained in the product reaction mixture resulting from step (b) can be separated and recovered from the product reaction mixture by conventional means such as fractional distillation. As demonstrated in examples to follow, the oligomerization product contains a desirable distribution of primarily $C_4$-$C_{10}$ oligomers.

Many variations of the invention are possible in the light of the above teachings. For example, although the invention is described above in terms of a batchwise process, it is within the scope of certain broad aspects of the invention to employ a continuous process wherein ethylene is passed continuously into a reaction zone while product reaction mixture containing the oligomerization product is concomitantly withdrawn therefrom.

An example of the invention is set forth below which should not be construed to limit the invention in any manner.

This example employed a 300 mL stainless steel (316SS) Autoclave Engineers stirred tank autoclave, hereafter denoted simply as a reactor. It is understood that the contents of such a reactor are being agitated, typically at a slow agitation of about 300 rpm during purging of the reactor or addition of various reagents to the reactor, and at a normal agitation of about 1600 rpm at all other times.

Product analysis was performed on approximately 5 gram samples with an HP 5890 II GC-FID Spectrometer equipped with a capillary DB-1 (60 m) column. The column was operated at 30° C. for 5 minutes, followed by a 15° C./minute increase to 285° C. which was held for 13 minutes. Detection was obtained using a flame ionization detector in the area percent mode. Selectivity and weight percent distribution, discussed further below, were determined from spectra as recorded by the spectrometer.

Results of the example are reported in terms of productivity, selectivity to 1-olefins and weight percent distribution of oligomerization product. Productivity is defined as the grams of oligomerization product produced per gram of Ni per hour, and was calculated based on grams of ethylene reacted. Selectivity to 1-olefins is given in terms of the weight percent of the $C_{10}$ fraction of the oligomerization product which is 1-decene. The distribution of the oligomerization product is given as the weight percent of the various fractions ($C_n$, n=4, 6, 8 . . . ) of the total oligomerization product.

EXAMPLE

This example illustrates ethylene oligomerization employing nickel(II) chloride hexahydrate, potassium trifluoroacetate, dicyclohexylphosphine, and sodium triethylborohydride in different solvents.

A reactor was purged with nitrogen for about 5 minutes followed by addition of 50 mL of a solvent indicated in Table I, nickel(II) chloride hexahydrate (0.238 g; 1.0 mmol), potassium trifluoroacetate (0.152 g; 1.0 mmol), and dicyclohexylphosphine (0.198 g; 1.0 mmol). The reactor was then sealed, purged with ethylene at least 4 times, and then pressured to 50 psig with ethylene at ambient temperature (about 25° C.) for about 5 minutes.

To a 40 mL addition vessel, connected to the reactor through an addition valve, was added 2 mL of a 1.0M solution of sodium triethylborohydride (2.0 mmol) in toluene by means of a syringe. The addition vessel was immediately sealed and pressured to 700 psig with ethylene. The contents of the addition vessel, including the ethylene, were then transferred to the reactor through the addition valve at the end of the above-mentioned 5 minute period. The internal reactor pressure was maintained at 700 psig and reactor temperature was maintained at 75° C. for a reaction period of 120 minutes.

At the end of the reaction period, a sample of the product reaction mixture was taken from the reactor through its sample valve into a 50 mL pressure sample tube, and was analyzed as described above. The resulting selectivity and weight distribution data, along with corresponding solvent and productivity, are set forth in the Table.

TABLE

| Run | Solvent | Productivity (g/g/hr) | Distribution Wt. % of $C_n$ (n = 4, 6, 8, 10, 12, 14 and higher) | Selectivity Wt. % of 1-decene |
|---|---|---|---|---|
| 1 | n-Propanol | 310 | 68, 20, 9, 3, 0, 0 | 72 |
| 2 | 2-Propanol | 190 | 65, 24, 8, 3, 0, 0 | 78 |
| 3 | Ethanol | 390 | 65, 21, 9, 4, 1, 0 | 79 |
| 4 | Phenol | 600 | 90, 9, 1, 0, 0, 0 | N/A |
| 5 | 1,4-Butanediol | 150 | 80, 14, 5, 1, 0, 0 | 70 |
| 6 | Trifluoroethanol | 110 | 52, 27, 12, 5, 2, 2 | 83 |
| 7 | 1,5-Pentanediol | 180 | 61, 24, 9, 4, 2, 0 | 86 |

The Table indicates that productivity ranges from 110 g/g/hr to 600 g/g/hr. Distribution of the oligomerization product varies among the solvents, but is mostly lower than $C_{12}$ olefins. Selectivity to 1-decene is at least 70% in each run in which $C_{10}$ olefins are present in the oligomerization product.

That which is claimed is:

1. A process for oligomerizing ethylene to an oligomerization product comprising:
   (a) contacting ethylene, a nickel(II) halide compound, a phosphine compound of the formula $PR_3$ where each R independently represents H or a $C_1$ to $C_{20}$ hydrocarbyl radical and where at least one R is not H, and a carboxylate compound of the formula R'COOM where R' is a $C_1$ to $C_{10}$ fluorinated hydrocarbyl radical having at least one fluorine atom and M is an alkali metal, wherein the ethylene is in a gaseous phase and the nickel(II) halide compound, phosphine compound, and carboxylate compound are in a solvent and in a liquid phase, thereby producing a precursor reaction mixture in a liquid phase; and
   (b) contacting, after step (a), ethylene in a gaseous phase, the precursor reaction mixture, and a borohydride compound of the formula $M'BH_{4-n}R_n''$ where n=1, 2, or 3, M' is an alkali metal, and each R" independently represents a $C_1$ to $C_{20}$ hydrocarbyl radical, thereby producing a product reaction mixture in a liquid phase comprising the oligomerization product.

2. A process as recited in claim 1 wherein step (a) is carried out at a pressure of about 5 to about 5000 psig, at a temperature of about 0° C. to about 100° C., and for a time of about 1 minute to about 2 hours.

3. A process as recited in claim 2 wherein step (a) is carried out at a pressure of about 20 to about 1000 psig, at a temperature of about 20° C. to about 75° C., and for a time of about 3 minutes to about 30 minutes.

4. A process as recited in claim 1 wherein step (b) is carried out at a pressure of about 5 to about 5000 psig, at a temperature of about 25° C. to about 125° C., and for a time of about 1 minute to about 15 hours.

5. A process as recited in claim 4 wherein step (b) is carried out at a pressure of about 200 to about 1000 psig, at a temperature of about 50° C. to about 100° C., and for a time of about 15 minutes to about 5 hours.

6. A process as recited in claim 1 wherein the nickel(II) halide compound is a nickel(II) chloride compound.

7. A process as recited in claim 6 wherein the nickel(II) chloride compound is nickel(II) chloride hexahydrate.

8. A process as recited in claim 1 wherein the phosphine compound is dicyclohexylphosphine.

9. A process as recited in claim 1 wherein the carboxylate compound is potassium trifluoroacetate.

10. A process as recited in claim 1 wherein in the borohydride compound of the formula $M'BH_{4-n}R_n''$, n=3 and R" is a $C_1$ to $C_{12}$ alkyl radical.

11. A process as recited in claim 10 wherein the borohydride compound is sodium triethylborohydride.

12. A process as recited in claim 1 wherein the molar ratio of (i) the phosphine compound, (ii) the carboxylate compound, and (iii) the borohydride compound, respectively, to the nickel(II) halide compound are as follows: (i) about 0.1–5 to 1; (ii) about 0.1–5 to 1; and (iii) about 1–10 to 1.

13. A process as recited in claim 1 wherein the solvent is a $C_1$ to $C_{12}$ hydroxylated hydrocarbon selected from the group consisting of an alcohol and a phenol.

14. A process as recited in claim 13 wherein the solvent is an alcohol.

* * * * *